USOO5627074A

United States Patent [19]

Mathis et al.

[11] Patent Number: 5,627,074
[45] Date of Patent: May 6, 1997

[54] METHOD OF REDUCING INTERFERENCE IN A FLUORESCENT ASSAY

[75] Inventors: Gérard Mathis, Bagnols sur Cèze; Christophe DuMont, Connaux; Etienne J. Jolu, Bagnols sur Cèze, all of France

[73] Assignee: CIS Bio International, Saclay, France

[21] Appl. No.: 956,487

[22] PCT Filed: Jul. 12, 1991

[86] PCT No.: PCT/FR91/00566

§ 371 Date: Sep. 16, 1994

§ 102(e) Date: Sep. 16, 1994

[87] PCT Pub. No.: WO92/01224

PCT Pub. Date: Jan. 23, 1994

[30] Foreign Application Priority Data

Jul. 13, 1990 [FR] France .................... 90 08982

[51] Int. Cl.⁶ .................. G01N 33/543; G01N 33/20; G01N 33/53
[52] U.S. Cl. .................. 436/518; 435/7.1; 435/7.2; 435/962; 436/81; 436/800
[58] Field of Search .................. 435/7.1, 7.2, 7.4, 435/962; 436/518, 800, 805, 81

[56] References Cited

U.S. PATENT DOCUMENTS 4,542,104 9/1985 Stryer et al. .................. 436/536

FOREIGN PATENT DOCUMENTS 0321353 6/1989 European Pat. Off.
9005302 5/1990 WIPO.

OTHER PUBLICATIONS

Journal of the American Chemical Society, vol. 102, No. 7, 26 Mar. 1980, American Chemical Society, E.L. Yee et al.; "Electrochemical Society of Europium and Ytterbium Cryptate Formation in Aqueous Solution. Effects of Varying the Metal Oxidation State upon Crypatate Thermodynamics and Kinetics", pp. 2278–2285, see abstract; p. 2284, column 2.

Primary Examiner—Toni R. Scheiner
Assistant Examiner—Yvonne Eyler
Attorney, Agent, or Firm—Marshall & Melhorn

[57] ABSTRACT

The invention relates to a method of reducing interference in a fluorescent assay of an analyte, which comprises adding fluoride ions to the measuring medium, and to its use in a fluorescent method of detecting and/or determining an analyte in a medium which may contain it.

20 Claims, 2 Drawing Sheets

METHOD OF REDUCING INTERFERENCE IN A FLUORESCENT ASSAY

The present invention relates to a method of reducing interference in a fluorescent assay.

At the present time, immunoassays are widely used for the qualitative and quantitative analysis of compounds in biological fluids.

Among the techniques in existence, fluorimetric assays have gained importance.

In fact, they have a number of advantages, including the sensitivity and speed of the measurement, the stability and safety of the reagents labeled with fluorescent compounds, and the relatively low cost.

It is known that methods of detection using fluorescence are intrinsically very sensitive and could permit lower detection limits than those attained by immunoassays using radiolabeled reagents, in particular by the use of modulatable laser light sources (I. Wieder, Immunofluorescence and related staining techniques, 1978, Elsevier).

Numerous fluorescent molecules usable as tracers in this type of assay have previously been described, among which rare earth complexes possess valuable properties.

The use of particular complexes, rare earth cryptates, is described in the following patent applications: EP 0 180 492, PCT/FR 86 00269, EP 0 321 353 or PCT/FR 89 00562.

These rare earth cryptates have the advantage of being very stable in a saline protein medium, this property being particularly important in the case of homogeneous immunoassays.

The sensitivity of the measurement can nevertheless be greatly affected by different types of interference resulting from the presence of various molecules in the medium in which the measurement is made.

This problem is particularly acute in the case of assays in a serum medium in which numerous molecules are capable of interfering.

For example, the measured signal can be subject to interference by emission from molecules capable of being excited and of emitting at the same wavelengths as the molecule used as the tracer.

The time-resolved methods of measuring fluorescence enable this disadvantage to be partially overcome. The principle of these methods consists in measuring the fluorescence emitted by a tracer molecule having a relatively long emission lifetime, the measurement being delayed in time beyond the emission lifetime of the other molecules present.

It is necessary in this case to use fluorescent tracer molecules with a relatively long lifetime, such as rare earth chelates.

The sensitivity of the measurement can also be affected by interference from molecules in the medium which are capable of perturbing the variation in fluorescence resulting from binding between the analyte to be detected and the labeled biospecific reagent. Patent application EP 0 324 323 describes the use of a modulator which stabilizes the rare earth chelate bound to the biospecific reagent, in such a way that the measured fluorescence is actually a function of the concentration of the analyte. The effect of this modulator is to prevent perturbation of the fluorescence of the rare earth chelate by the other molecules present in the medium. The measured variation in fluorescence is then a function only of the antigen-antibody reaction. The proposed modulators are macro-molecules, such as proteins and detergents, and have to be used in excess in the range from 0.1 to 10 g/l.

Nevertheless, the problem of the interference due to the molecules present in the measuring medium is not completely solved by any of these methods. In fact, an important source limiting the sensitivity of the fluorescent measurement is the existence of quenching processes due to molecules present in the medium which are capable of inhibiting the fluorescence of the fluorescent molecule used as the marker in the assay. In the case of rare earth complexes, these processes can result from proximity electron transfer mechanisms, where the inhibitor molecule occupies the coordination sites remaining free within the complex. In particular, there may be mentioned the redox reactions taking place between the fluorescent molecule and molecules present in the medium. These mechanisms are capable of varying the emitted fluorescence significantly.

The inhibition of fluorescence due to redox phenomena is not described in the literature relating to homogeneous immunofluorescent assays.

The article by Weber et al., Clin. Chem., 1993, 29/9, 1665–1672, describes the influence of interference, due in particular to uric acid, in the ampero-metric detection of a tris(2',2'-bipyridine)ruthenium-(III) complex. This complex originates from the redox reaction of the corresponding Ru(II) complex, which is capable of oxidising a Co(III) quencher complex. Uric acid has been identified as a reducing agent for Ru(III) and is therefore capable of interfering in the measurement.

This redox mechanism, due to an electron transfer between a fluorescent compound and a quencher compound, has also been demonstrated by Sabbatini et al., J.A.C.S., 1984, 106, 5044–4056. This article especially describes the oxidation of an $M(CN)_6^{4-}$ complex, in which M is iron, ruthenium or osmium, by a europium cryptate.

The inhibition of fluorescence by mechanisms involving an electron transfer, and by quenching mechanisms in general, is an extremely troublesome phenomenon in practice because the inhibitory factors can either be naturally present as components in the measuring medium (for example uric acid in serum) or else be added thereto as additives or stabilizers for the assay.

These inhibitors greatly affect the fluorescence of the marker molecule. In particular, in the case of parasitic redox reactions, the conversion of a rare earth ion from the reduced state to the oxidized state by way of a redox mechanism decreases the lifetime and modifies the emission spectrum of the complex containing said ion, thereby greatly affecting the sensitivity of the measurement.

Unexpectedly, it has now been found that the addition of fluoride ions to the measuring medium makes it possible substantially to reduce the inhibition of fluorescence due to the presence of inhibitor molecules in this medium.

In particular, this interference is notably reduced in a biological medium.

Surprisingly, it has also been found that these fluoride ions do not adversely affect the stability of the rare earth cryptate complexes used, in contrast to the description in Yee et al., J.A.C.S., 1980, 102, 2278–2285, where the association of fluoride ions in a trivalent rare earth cryptate resulted in a substantial acceleration of the rate of dissociation of the cryptate, the half-life of the product dropping from 27 days to 2.8 days.

It has in fact been observed that by adding fluoride ions to the measuring medium, in particular in the form of sodium fluoride, the lifetime of the signal emitted by a rare earth cryptate or chelate used as the tracer molecule becomes comparable again to that of the signal measured in the buffer alone.

By way of a hypothesis, it is possible to consider that, by virtue of their small size and their negative charge, the fluoride ions can occupy the free binding sites in the rare earth complexes and thus prevent inhibitors from gaining access.

The invention therefore relates to a method of reducing interference in a fluorescent assay of an analyte using at least one fluorescent compound as the tracer, which comprises adding fluoride ions to the measuring medium.

In the present description:

"analyte" defines any substance or group of analogous substances to be detected and/or determined;

"receptor" defines any substance capable of binding specifically to a site on said analyte.

According to a preferred feature, the measuring medium is a biological medium such as a serum medium.

It will be advantageous to use sodium, cesium, potassium or lithium fluoride if the measuring medium is an aqueous medium. The choice of cation will depend on the medium used and will be chosen so that the fluoride ions are soluble in the medium, this choice being within the scope of those skilled in the art.

In particular, sodium fluoride (NaF) will be used at a concentration of 50 to 500 mM/l in a serum medium.

According to another advantageous feature, potassium fluoride (KF) will be used at a concentration of 50 mM/l to 5M/l.

A rare earth chelate or cryptate will advantageously be used as the fluorescent tracer compound.

Rare earth ions which can be used in particular are terbium, europium, dysprosium, samarium or neodymium ions. Terbium or europium will preferably be used.

The method according to the invention can advantageously be used for reducing interference in the measuring medium during a fluorescent method of detecting and/or determining an analyte in a medium which may contain it.

The method of the invention has an important application in fluorescent immunoassays, in either the so-called competitive or excess assay methods, in the homogeneous or heterogeneous phase, which have been described in the prior art (Landon, Ann. Clin. Biochem., 1981, 18, 253, and E. SOINI et al., Clin. Chem., 1979, 25, 353).

In particular, the method of detecting and/or determining the analyte is a homogeneous method.

According to a preferred feature, the method of the invention for reducing interference can be used in a fluorescent method of detecting and/or determining an analyte in a medium which may contain it, consisting in:

1) adding to said medium a first reagent constituted of at least one receptor for said analyte,
2) adding a second reagent selected from the analyte or at least one of its receptors, one of the two reagents being coupled with a fluorescent donor compound and the other reagent being coupled with a fluorescent acceptor compound, and the order of addition of the reagents being reversible.
3) incubating the resulting medium either after the addition of each reagent or after the addition of both reagents,
4) exciting the resulting medium at the excitation wavelength of the donor compound, and
5) measuring, at equilibrium or under kinetic conditions, the signal emitted by the fluorescent acceptor compound.

According to an advantageous feature, the method of the invention will be used in a fluorescent method of detecting and/or determining an analyte in a medium which may contain it, with the aid of an excess method consisting in:

1) adding, to said medium containing the analyte in question, a first reagent consisting of at least one receptor for said analyte, coupled with a fluorescent donor compound,
2) adding a second reagent consisting of one or more other receptors for said analyte, said second reagent being coupled with a fluorescent acceptor compound,
3) incubating said medium either after the addition of each reagent or after the addition of both reagents,
4) exciting the resulting medium at the excitation wavelength of the fluorescent donor compound by means of a light source, and
5) measuring the signal emitted by the fluorescent acceptor compound.

According to a preferred feature, the above excess method will be carried out using a single receptor for the analyte, which is coupled either with the fluorescent donor compound or with the fluorescent acceptor compound.

The method according to the invention can also be used in a fluorescent method of detecting and/or determining an analyte in a medium which may contain it, with the aid of a competitive method consisting in:

1) adding, to said medium containing the analyte in question, a first reagent consisting of a receptor for said analyte, coupled with a fluorescent donor compound,
2) adding a second reagent made up of the analyte coupled with a fluorescent acceptor compound,
3) incubating said medium either after the addition of each reagent or after the addition of both reagents,
4) exciting the resulting medium at the excitation wavelength of the fluorescent donor compound, and
5) measuring the signal emitted by the fluorescent acceptor compound.

The method according to the invention for reducing interference can also be used in a fluorescent method of detecting and/or determining an analyte in a medium which may contain it, with the aid of a competitive method consisting in:

1) adding, to said medium containing the analyte in question, a first reagent consisting of a receptor for said analyte, said receptor being coupled with a fluorescent acceptor compound,
2) adding, as a second reagent, the analyte being coupled with a fluorescent donor compound,
3) incubating said medium either after the addition of each reagent or after the addition of both reagents,
4) exciting the resulting medium at the excitation wavelength of the fluorescent donor compound, and
5) measuring the signal emitted by the fluorescent acceptor compound.

According to an advantageous feature, the first reagent and second reagent used in the fluorescent methods of detecting and/or determining an analyte, indicated above, are added simultaneously to the medium containing the analyte in question.

In the fluorescent methods of detection and/or determination using the method of the invention for reducing interference, a rare earth chelate or cryptate, in particular the cryptates described in patent applications EP 180 492 and 321 353, will advantageously be chosen as the fluorescent donor compound.

The fluorescent donor compound is preferably the terbium cryptate Tb trisbipyridine or the europium cryptate Eu trisbipyridine, as described in patent application EP 180 492.

According to an advantageous feature, the fluorescent donor compound is a europium cryptate and the fluorescent acceptor compound is selected from allophycocyanin, allophycocyanin B, phycocyanin C or phycocyanin R.

It is also possible to use a terbium cryptate as the fluorescent donor compound and a compound selected from rhodamines, thionine, phycocyanin R, phycoerythrocyanin, phycoerythrin C, phycoerythrin B or phycoerythrin R as the fluorescent acceptor compound.

The invention will be understood more clearly with the aid of the Examples below, which in no way imply a limitation.

In the Examples which follow, the europium cryptate Eu trisbipyridinediamine is prepared as described in patent application EP 21 353 (Examples 3 and 4).

The following abbreviations are used hereafter:

APC=allophycocyanin

DTT=dithiothreitol

Eu TBP=europium cryptate Eu trisbipyridinediamine

HSA=human serum albumin

IgG=immunoglobulin G

N-AANS=N-acetyl-8-anilinonaphthalene-1-sulfonic acid

S-AMSA=S-acetylmercaptosuccinic anhydride

SPDP=N-succinimidyl 3-(pyridin-2-yldithio)propionate

Sulfo-SMCC=sulfosuccinimidyl (4-N-maleimidomethyl) cyclohexane-1-carboxylate $T_4$=thyroxin

EXAMPLE 1

Effect of sodium fluoride (NaF) on the emission lifetime of the europium cryptate Eu trisbipyridinediamine in a serum medium To evaluate the effect of sodium fluoride on the lifetime of the signal emitted by the europium cryptate Eu trisbipyridinediamine, the first step was to prepare an antibody/europium cryptate conjugate, identical to the conjugates which can be used in a homogeneous immunoassay, by coupling the europium cryptate with an anti-prolactin $E_1$ monoclonal antibody (CIS bio international, France). The emission lifetime of this conjugate was then measured in a phosphate buffer medium and in a serum medium in the presence of different concentrations of NaF.

A/Preparation of the antibody/europium cryptate Eu trisbi-pyridinediamine conjugate a) Activation of the cryptate Eu TDP with sulfo-SMCC A 25 mM solution of sulfo-SMCC in 20 mM phosphate buffer, dimethylformamide 10% (v/v), pH 7.0, is added to 5 mg ($5.10^{-6}$ mol) of Eu TBP in a proportion of 2.5 mol of activator per mol of Eu TBP.

After activation for 45 min at room temperature, the reaction medium is filtered on a 0.8 µm filter to remove any precipitate formed. The undesirable reaction products (sulfo-SMCC, N-hydroxysuccinimide, (N-maleimidomethyl)carboxylic acid) are removed by ion exchange chromatography on a column (Mono Q) (Pharmacia, Sweden) in 20 mM phosphate buffer, dimethylformamide 10% (v/v), pH 7.0, under NaCl shock. The concentration of Eu TBP-maleimide is determined at 307 nm with $\epsilon_{307nm}$=25,000 $M^{-1}.cm^{-1}$.

b) Activation of the IgG $E_1$ with SPDP

Simultaneously, 5 mg of IgG $E_1$, at a concentration of 10 mg/ml in 100 mM phosphate buffer, pH 7.0, are activated by the addition of a solution of SPDP (Pierce, USA), at a concentration of 6.4 mM in dioxane, in a molar ratio of 4 to 16 SPDP per IgG $E_1$.

After activation for 35 min at room temperature, the IgG-pyridine-2-thione is purified on a G25 superfine column in 100 mM phosphate buffer, EDTA 5 mM, pH 6.5.

The proteins are concentrated and the pyridin-2-yl disulfide groups are reduced with a solution of DDT (Sigma, USA), having a final concentration of 19 mM, for 15 min at room temperature. The DDT and pyridine-2-thione are removed by purification on a G25 superfine column (Pharmacia, Sweden) in 100 mM phosphate buffer, EDTA 5 mM, pH 6.5. The concentration of IgG-SH is determined at 280 nm with $\epsilon_{280nm}$=210,000 $M^{-1}.cm^{-1}$.

c) Conjugation of the IgG $E_1$ with Eu TBP-maleimide

The thiol groups are bound to the maleimides in molar proportions of 10 to 30 Eu TBP-maleimide per IgG $E_1$-SH. After incubation for 18 hours at 4° C. in the dark, with gentle agitation, the thiol groups which have remained free are blocked by the addition of a 100 mM solution of N-methylmaleimide (Sigma, USA), having a final concentration of 20 mM, for one hour at room temperature. The non-coupled Eu TBP is then removed by dialysis in 100 mM phosphate buffer, pH 7.0, at 4° C. to the point of exhaustion (no more fluorescence in the dialysis baths).

The characteristics of the conjugate are determined by its absorptions at 307 nm and 280 nm using the following values, taking into account the inherent absorption of the cryptate Eu TBP determined by the experimentally evaluated ratio $A_{307nm}/A_{280nm}$:

Eu TBP-maleimide:

$\epsilon_{307nm}$=25,000 $M^{-1}.cm^{-1}$

IgG $E_1$-SH:

$\epsilon_{280nm}$=210,000 $M^{-1}.cm^{-1}$ $\epsilon_{307nm}$=0 $M^{-1}.cm^{-1}$ B/Measurement of the emission lifetime of the antibody/europium cryptate conjugate in water and in a serum medium in the presence of NaF The IgG $E_1$/Eu TBP conjugate prepared as described above is diluted to 1/250 in a 100 mM phosphate buffer, pH 7, containing 1 g/l of human serum albumin (HSA) and variable concentrations of sodium fluoride (NaF).

200 µl of this solution are added to 100 µl of newborn calf serum or phosphate-buffer. The lifetime of the conjugate is then measured at 620 nm with the aid of a laser fluorimeter (prototype) as described below:

A nitrogen pulsed laser (LASER SCIENCE INC., model LS1-337ND) is used as the excitation source (wavelength at 337.1 nm). The pulse duration is specified at 3 nanoseconds and is repeated at a frequency of 10 Hertz. The beam passes through a filter (CORNING) to remove any light interfering with the excitation, other than 337 nm.

After entering the measuring chamber, the beam is reflected by a dichroic filter, placed at 45 degrees, which has the property of reflecting the ultraviolet and of being able to transmit the visible light.

The beam reflected by the dichroic filter is focused by a fused silica lens on to the well to be measured in a microplate. The fluorescence emission is collected at a solid angle of 20 degrees, collimated by the same lens, and passes directly through the dichroic filter (visible light fluorescence).

An interference filter, the characteristics of which are defined according to the fluorescence wavelength to be detected, makes it possible to remove the light capable of interfering with the signal, the intensity of which is then measured by a photomultiplier (HAMAMATSU R2949).

The photon counter used is an SR-400 (STANFORD RESEARCH SYSTEMS), whose operations and synchronization with the laser are controlled by a computer of the IBM PC-AT type via an RS 232 output. The pulses coming from the photomultiplier are recorded over a given time window ($t_g$) and after a given delay ($t_d$), provided they are above a discriminant level selected by the photon counter so as to optimize the signal-to-noise ratio of the photomultiplier.

An X-Y table, driven by the IBM PC-AT, uses step motors to set up the different positions of the measuring microplate, including the maneuvers of charging, positioning underneath the exciting beam, automatic sequential reading of the 96 wells, and exiting.

It is also possible to use an ARCUS fluorimeter (LKB, Sweden) with an interference filter adapted to the emission of the fluorescent compound.

The measurement is made over a time window ($t_g$) of 100 μsec and after a delay ($t_d$) of 50 to 600 μsec.

The results are reported in Table I below:

TABLE I

| NaF mM | τ phosphate buffer ms | τ serum ms |
|---|---|---|
| 0 | 0.64 | 0.38 |
| 100 | 0.80 | 0.64 |
| 150 | 0.81 | 0.69 |
| 200 | 0.83 | 0.70 |
| 225 | 0.83 | 0.72 |
| 300 | 0.85 | 0.73 |
| 500 | 0.90 | 0.78 |

τ = lifetime of the emitted signal

The results show that the lifetime in a serum medium is considerably increased by the presence of NaF in the medium. As from a concentration of 500 mM of NaF in the conjugate solution, the lifetime of the conjugate is doubled relative to that of the conjugate in a serum medium without NaF.

EXAMPLE 2

Effect of potassium fluoride (KF) on the emission lifetime of the europium cryptate Eu trisbipyridinediamine in a serum medium The IgG $E_1$/Eu TBP conjugate prepared as described in Example 1 is diluted to 1/250 in 100 mM phosphate buffer, pH 7, containing 1 g/l of human serum albumin (HSA) and variable concentrations of potassium fluoride.

200 μl of this solution are added to 100 μl of newborn calf serum. The measurement is made under the operating conditions of Example 1.

The results are reported in Table II below:

TABLE II

| KF mM | τ serum ms |
|---|---|
| 0 | 0.41 |
| 100 | 0.76 |
| 200 | 0.90 |
| 400 | 1.01 |

τ = lifetime of the emitted signal

The results show that the lifetime in a serum medium is significantly increased by the presence of KF in the measuring medium.

EXAMPLE 3

Effects of different additives in different media on the lifetime of the europium cryptate Eu trisbipyridinediamine in the presence of NaF The media used are newborn calf serum and human serum (serum pool).

The IgG 3D3/Eu TBP conjugate (prepared analogously to the IgG $E_1$/Eu TBP conjugate of Example 1 by coupling the europium cryptate with the antiprolactin 3D3 monoclonal antibody (CIS bio international, France)) is used at a concentration of 0.5 μg/ml in 100 mM phosphate dilution buffer, pH 7, NaF 150 mM, HSA 1 g/l.

A sample is prepared which contains 100 μl of serum, 100 μl of antibody/cryptate conjugate and 100 μl of buffer containing variable concentrations of the following different additives: EDTA, $NaN_3$ and merthiolate.

The lifetime of the antibody/cryptate conjugate is measured at 620 nm with the aid of an Arcus apparatus (LKB, Sweden) over 100 μs and after a delay of 50 to 600 μs.

For each assay, the values obtained without an additive for the antibody/cryptate conjugate by itself are determined by way of reference: the sample then contains 100 μl of serum, 100 μl of antibody/cryptate conjugate and 100 μl of buffer without additive. The results obtained are given in Table III below:

TABLE III

| Additive | Final concentration | τ ms |
|---|---|---|
| Newborn calf serum | | |
| EDTA | 0 | 0.76 |
| | 5 g/l | 0.76 |
| | 1 g/l | 0.78 |
| | 0.5 g/l | 0.78 |
| | 0.1 g/l | 0.78 |
| $NaN_3$ | 0 | 0.76 |
| | 1 g/l | 0.75 |
| | 0.5 g/l | 0.75 |
| | 0.1 g/l | 0.75 |
| Merthiolate | 0 | 0.76 |
| | 40 mg/l | 0.79 |
| | 20 mg/l | 0.76 |
| | 10 mg/l | 0.77 |
| | 5 mg/l | 0.76 |
| Human serum (pool) | | |
| EDTA | 0 | 0.65 |
| | 5 g/l | 0.71 |
| | 1 g/l | 0.67 |
| | 0.5 g/l | 0.66 |
| | 0.1 g/l | 0.66 |
| $NaN_3$ | 0 | 0.65 |
| | 5 g/l | 0.69 |
| | 1 g/l | 0.68 |
| | 0.5 g/l | 0.68 |
| | 0.1 g/l | 0.66 |
| Merthiolate | 0 | 0.65 |
| | 40 mg/l | 0.66 |
| | 20 mg/l | 0.66 |
| | 10 mg/l | 0.67 |
| | 5 mg/l | 0.66 |

The results show that the addition of sodium fluoride to the measuring medium makes it possible to keep the lifetime of the conjugate virtually constant, irrespective of the additive and its concentration.

EXAMPLE 4

Assay of prolactin

A homogeneous immunoassay was performed using the assay of prolactin as a model.

This assay used anti-prolactin $E_1$ and 3D3 monoclonal antibodies (CIS bio international) recognizing 2 distinct epitopes of prolactin, coupled respectively to the europium cryptate Eu trisbipyridinediamine and to allophycocyanin (Cyanotech, USA).

A) PREPARATION OF THE IgG 3D3/APC a) Activation of the APC with sulfo-SMCC

APC (3 mg), supplied commercially in the form of a precipitate in a 60% solution of ammonium sulfate, is centrifuged. After removal of the supernatant, the residue is taken up with 250 µl of 100 mM phosphate buffer, pH 7.0, and the solution is then filtered on a 0.8 µm filter to remove any suspended particles.

The filtrate is purified by exclusion chromatography on a G25 superfine column (Pharmacia, Sweden) in the same buffer. The concentration of APC eluted in the exclusion volume is determined at 650 nm, taking into account that $\epsilon_{650nm} = 731{,}000$ $M^{-1}.cm^{-1}$.

The APC is activated by adding a solution of sulfo-SMCC, at a concentration of 6.9 mM in 100 mM phosphate buffer, pH 7.0, prepared for immediate use, and by allowing the reaction to proceed for 1 h at room temperature, with gentle agitation (molar ratio of 15 to 75 sulfo-SMCC per APC). The APC-maleimide is then purified on a G25 superfine column in 100 mM phosphate buffer, EDTA 5 mM, pH 6.5, and kept at 4° C. before coupling with IgG 3D3.

b) Activation of the IgG 3D3 with SPDP

Simultaneously, 5 mg of IgG 3D3, at a concentration of 10 mg/ml in 100 mM phosphate buffer, pH 7.0, are activated by the addition of a solution of SPDP (Pierce, USA), at a concentration of 6.4 mM in dioxane, in a molar ratio of 7.5 SPDP per IgG 3D3.

After activation for 35 min at room temperature, the IgG-pyridine-2-thione is purified on a G25 superfine column in 100 mM phosphate buffer, EDTA 5 mM, pH 6.5.

The proteins are concentrated and the pyridin-2-yl disulfide groups are reduced with a solution of DTT (Sigma, USA), having a final concentration of 19 mM, for 15 min at room temperature. The DTT and pyridine-2-thione are removed by purification on a G25 superfine column in 100 mM phosphate buffer, EDTA 5 mM, pH 6.5. The concentration of IgG-SH is determined at 280 nm with $\epsilon_{280nm} = 210{,}000$ $M^{-1}.cm^{-1}$.

c) Conjugation of the IgG 3D3-SH with APC-maleimide

The thiol groups are bound to the maleimides by adding 2.51 mg of activated APC per mg of IgG 3D3-SH. After incubation for 18 h at 4° C. in the dark, with gentle agitation, the thiol groups which have remained free are blocked by the addition of a 100 mM solution of N-methylmaleimide (Sigma, USA), having a final concentration of 20 mM, for 1 h at room temperature.

The reaction medium is purified by gel filtration on a semipreparative TSK G3000SW column (Beckmann, USA) in 100 mM phosphate buffer, pH 7.0.

The concentrations of APC and IgG 3D3 in the purified conjugate eluted in the first peak are determined by the absorptions at 280 nm and 650 nm according to the following calculation:

$$[APC]_{mol/l} = A_{650nm} / 710{,}000$$

$$[IgG]_{mol/l} = (A_{280nm} - A'_{280nm}) / 210{,}000$$

where $A'_{280nm}$ is the contribution of the APC-maleimide at this wavelength, determined above (section A-a)).

Human serum albumin (HSA) is added to the conjugate in an amount of 1 g/l, after which the conjugate is divided up into aliquots and then frozen at −20° C.

B) PREPARATION OF THE IgG $E_1$/Eu TBP CONJUGATES

These conjugates are prepared according to the protocol described in Example 1.

C) APPLICATION TO THE ASSAY OF PROLACTIN

The labeled antibodies prepared as described above are used under the following conditions:

IgG $E_1$ labeled with the europium cryptate Eu trisbipyridinediamine at a concentration of 1 µg/ml in 100 mM phosphate buffer, NaF 150 mM, HSA 1 g/l, pH 7.

IgG 3D3 labeled with allophycocyanin (Cyanotech, USA) at 2.5 µg/ml in the same buffer.

The prolactin standards are made up in different media:

the above buffer a pool of human sera a standard range prepared in newborn calf serum.

The sample volume is 100 µl of each conjugate are added and the mixture is incubated for 60 minutes at room temperature in 96-well polystyrene microplates (Dynatech, USA).

The results are read on the laser fluorimeter (prototype) described in Example 1. This fluorimeter is equipped with a 655 nm filter with a width at half-height of 20 nm using a nitrogen pulsed laser as the excitation source, over a time window ($t_g$) of 100 µs and after a delay ($t_d$) of 50 µs.

Figure 1:
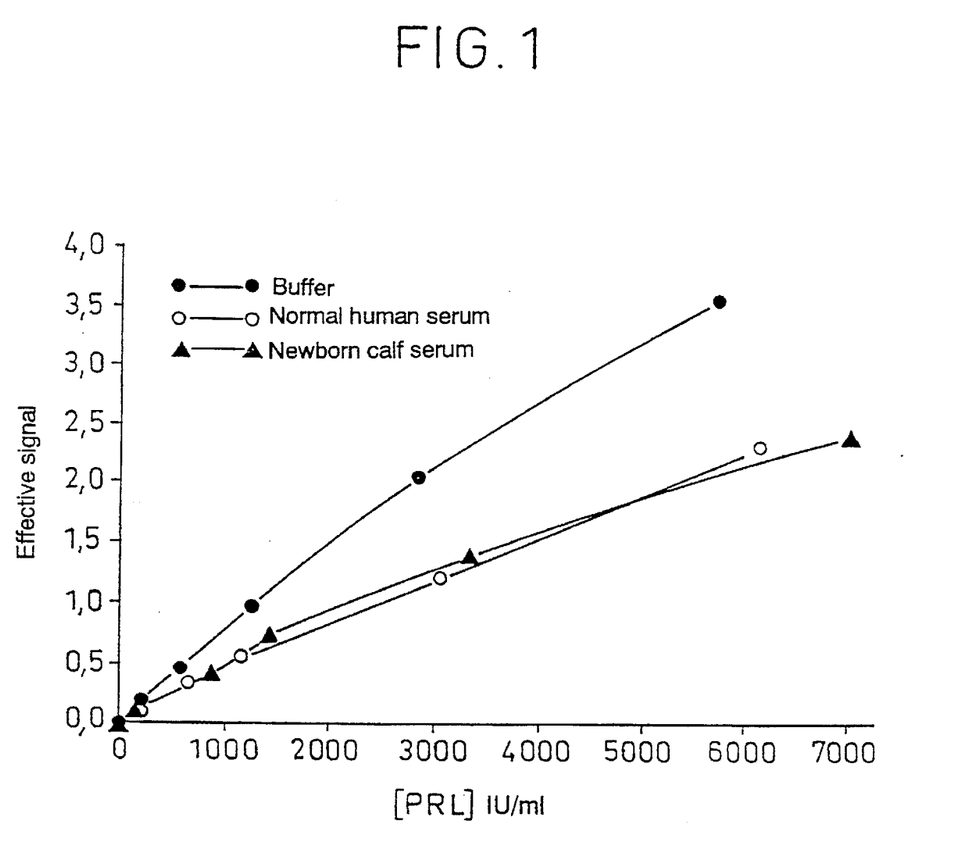
FIG. 1 depicts the assay and measurement of the fluorescence of prolactin. The amount of prolactin in IU/ml is plotted on the abscissa and the effective signal is plotted on the ordinate.

The results are shown in FIG. 1, in which the amount of prolactin in IU/ml is plotted on the abscissa and the effective signal ΔF, determined by:

$$\Delta F = \frac{\text{fluorescence of the measured standard} - \text{fluorescence of the standard 0}}{\text{fluorescence of the standard 0}},$$

is plotted on the ordinate.

The results show that the assay can be performed by virtue of the presence of sodium fluoride, despite the presence of fluorescence-inhibiting serum factors.

EXAMPLE 5

Assay of prolactin

Another homogeneous immunoassay using the assay of prolactin as a model was performed with potassium fluoride (KF) in the measuring medium.

The labeled antibodies prepared as described in Example 4 are used under the following conditions:

IgG $E_1$ labeled with the europium cryptate Eu trisbipyridinediamine at a concentration of 1 µg/ml in 100 mM phosphate buffer, KF 600 mM, HSA 1 g/l, pH 7.

IgG 3D3 labeled with allophycocyanin (Cyanotech, USA) at 2.5 µg/l in the same buffer.

The prolactin standards are made up in newborn calf serum.

The assay and the measurement of the fluorescence are carried out under the conditions described in Example 4, but the results are read over a time window ($t_g$) of 400 µs and after a delay ($t_d$) of 50 µs.

Figure 2:
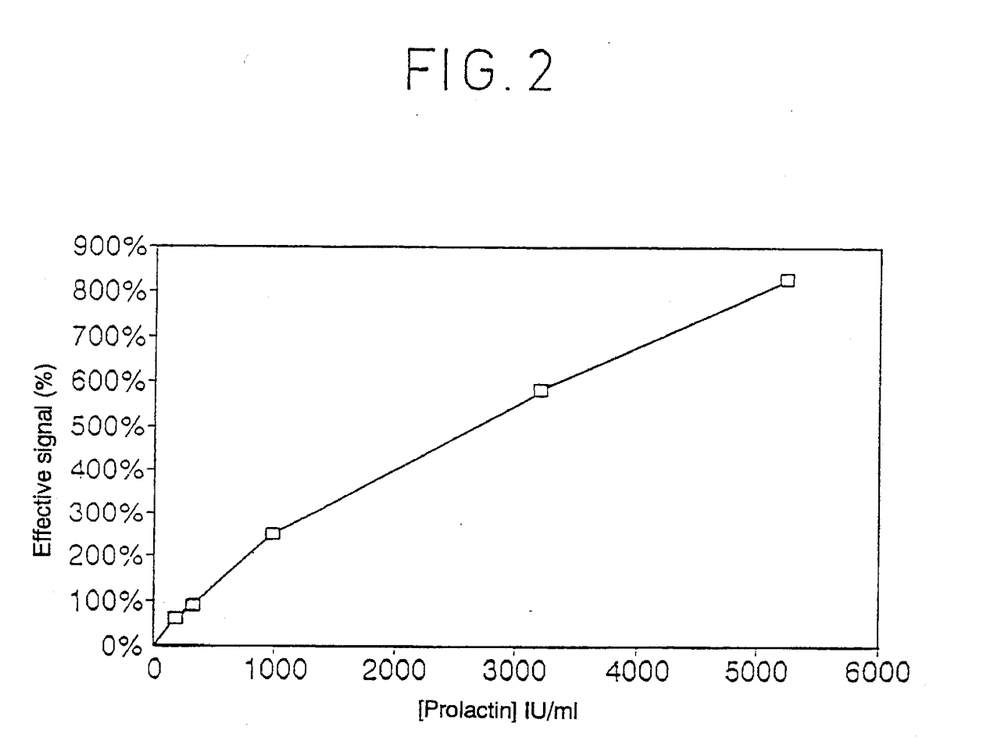
FIG. 2 depicts the assay and measurement of the fluorescence of prolactin. The amount of prolacting in IU/ml is plotted on the abscissa and the effective signal is plotted on the ordinate.

The results are given in FIG. 2, in which the amount of prolactin in IU/ml is plotted on the abscissa and the effective signal, determined as in Example 4, is plotted on the ordinate.

The results show that the presence of potassium fluoride in the medium ensures the sensitivity of the assay, despite the presence of fluorescence-inhibiting serum factors.

EXAMPLE 6

In an assay analogous to that described in Example 2 above, the effect of sodium fluoride at a final concentration of 100 mM was also tested on 50 human sera using a 3D3 antibody/Eu trisbipyridine cryptate conjugate.

The results obtained show that the lifetime of the antibody/cryptate conjugate is constant, contrary to what is observed in practice in this type of assay in a serum medium.

EXAMPLE 7

Assay of digoxin

Digoxin is a cardiotonic glucoside used as the active principle of drugs for treating cardiac insufficiency.

A/Preparation of an allophycocyanin-digoxin tracer by coupling with periodate a) Activation of the digoxin with periodate 268 µl of a solution of $NaIO_4$ (Fluka, Switzerland), prepared for immediate use, are added to a suspension of digoxin (ref. 37100 Fluka, Switzerland) containing 5.35 mg in 268 µl of absolute ethanol.

The mixture is incubated for 20 min at room temperature, with agitation, and the reaction is then blocked by the addition of 100 µl of 0.1M glycerol.

The final concentration of activated digoxin, calculated relative to the initial weight and the final volume, is $1.2 \times 10^{-2}$M.

b) Coupling of the activated digoxin with allophycocyanin (APC)

95 µl of the solution of digoxin activated with periodate are added to 2 ml of purified APC solution (Cyanotech, USA) in borate buffer, pH 9.0.

The mixture is incubated for 1 h 30 min at room temperature, with gentle agitation. The reaction is blocked by the addition of 100 µl of a solution of sodium borohydride at a concentration of 5 mg of $NaBH_4$ in 1.32 ml of borate buffer, pH 9.0, prepared for immediate use.

c) Purification of the APC-digoxin tracer 2 ml of the reaction mixture are injected on to an HR 10/10 G25 column (Pharmacia, Sweden), equilibrated in 100 mM phosphate buffer, pH 7, and eluted in the excluded volume. The excess reagents are eluted with 8 ml of buffer.

About 4 ml of a solution of APC-digoxin coupled product, containing 1.22 mg/ml of APC (measured by the absorbance at 650 nm), are recovered.

The concentration of digoxin is evaluated by RIA or DELFIA (Pharmacia, Sweden).

The calculated final molar ratio digoxin/allophycocyanin is about 0.8.

B/Competitive homogeneous assay of digoxin in human serum

An antibody/europium cryptate Eu TBP diamine conjugate is prepared in a manner analogous to that described in Example 1, using an anti-digoxin mouse monoclonal antibody (ref. G 31604M, Interchim, France). This antibody/cryptate conjugate is used at a concentration of 0.5 µg/ml in 100 mM phosphate buffer, NaF 150 mM, HSA 1 g/l, pH 7.

The APC-digoxin tracer is used at a concentration of 0.2 µg/ml in the same buffer.

A range of digoxin standards is prepared by diluting a solution of digoxin (Fluka, Switzerland), at a concentration of 1 mg/ml in a 50/50 ethanol/water mixture, in human serum.

The standard curve is drawn up with the aid of 250 µl samples containing

50 µl of phosphate buffer

50 µl of standard

100 µl of APC-digoxin tracer

100 µl of antibody/cryptate conjugate

The samples to be assayed have the same composition except that the 50 µl of standard are replaced with 50 µl of individual serum to be assayed.

The assay is performed in 96-well microplates (Dynatech, USA).

After incubation for 30 min at room temperature, the results are read on a laser fluorimeter such as that described in Example 1, equipped with a 665 nm filter with a width at half-height of 20 nm, over a time window of 100 µs and after a delay of 50 µs.

The results are expressed as a percentage of the ratio $B/B_o$, where B represents the value obtained for each standard and $B_o$ the value obtained for the standard 0.

The results obtained are reported in Table IV below:

TABLE IV

| Digoxin standard ng/ml | $B/B_o$ % |
|---|---|
| 0 | 100 |
| 1.6 | 96.21 |
| 3.2 | 87.15 |
| 6.4 | 73.57 |
| 12.8 | 56.24 |
| 26 | 48.86 |

These results show that the values obtained vary proportionately to the concentration of digoxin. The presence of sodium fluoride in the measuring medium makes it possible to perform the assay of digoxin in a serum medium with a sensitivity of the order of ng/ml.

EXAMPLE 8

Assay of thyroxin

A Preparation of an allophycocyanin-thyroxin (APC-$T_4$) tracer a) Activation of the thyroxin with S-AMSA 500 µl of a solution of S-AMSA (Sigma, USA) containing 8.7 mg/ml (50 mM) in methanol are added to 500 µl of a solution containing 20 mg/ml of $T_4$ (Calbiochem, France) in methanol, and the mixture is incubated for 15 min at room temperature before the addition of 500 µl of a solution of hydroxylamine containing 6.95 mg/ml (100 mM) in methanol. After incubation for 15 min at room temperature, 975 µl of the reaction mixture are removed and 525 µl of double-distilled water, filtered on a MILLIPORE HA 0.45 µm filter, are added. This solution is passed in 250 µl portions over a Pep.RPC HR 5/5 HPLC column (Pharmacia, Sweden) and eluted with a 65/35 methanol/water mixture. The first three peaks eluted are recovered and the successive fractions are combined and evaporated under vacuum in a rotary evaporator. About 3 mg of activated $T_4$ ($T_4$-SH) are recovered.

b) Activation of the allophycocyanin with SMCC 10 mg of APC are purified and then concentrated on an AMICON CENTRICON 30 cone to a concentration of 10.6 mg/ml in a volume of 700 µl.

160 µl of a solution of sulfo-SMCC (Pierce, USA) containing 10 mg/ml in a 100 mM phosphate buffer, pH 7, are added to this solution. The reaction mixture is incubated for 1 h at room temperature, with agitation, and the activated APC is then purified by exclusion chromatography on a G25 HR 10/10 column (Pharmacia, Sweden) in phosphate buffer, pH 7.

c) Coupling of the activated thyroxin with the activated allophycocyanin

The contents of the $T_4$-SH flask are taken up with 200 µl of methanol and 50 µl of this solution are added to 2 ml of activated APC solution in 100 mM phosphate buffer, pH 7. The reaction mixture is incubated for 18 h at 4° C., with agitation, and the excess maleimide sites are then blocked with 5 µl of a solution of mercaptoethanol (Sigma, USA) at 1/10 in phosphate buffer.

d) Purification of the APC-$T_4$ tracer

The reaction mixture is concentrated to a volume of 1 ml on an AMICON CENTRICON 30 ultrafiltration device and 50 µl of a solution of N-AANS containing 1 mg/ml in phosphate buffer are then added (final concentration of N-AANS about 50 g/ml). The tracer is finally purified on a PHARMACIA G25 HR 10/10 exclusion chromatography column (100 mM phosphate elution buffer, pH 7) to give about 2.5 ml of tracer at a concentration of 0.8 mg/ml (calculated via OD at 650 nm, $\epsilon$=731,000).

The number of molecules of $T_4$ coupled per molecule of APC is evaluated by RIA of the tracer and comparison with a $T_4$ standard curve ($T_4$-KPR kit, ORIS Industrie, France). The calculation gives a ratio relative to the purified tracer of 1.4 $T_4$/APC.

The APC-$T_4$ tracer is purified in the presence of N-AANS synthesized from N-ANS (KODAK, USA) by a modified version of the protocol described by HINDS et al. (CLIN. CHEM., 32, 16–21, 1986).

B/Competitive homogeneous assay of thyroxin in human serum

An antibody/Eu TBP diamine europium cryptate conjugate is prepared in a manner analogous to that described in Example 1, using an anti-$T_4$ $R_{41}$ mouse monoclonal antibody (CIS bio international, France). This conjugate is used at a concentration of 2 g/ml in 100 mM phosphate buffer, NaF 120 mM, HSA 0.2%, pH 7.

A range of $T_4$ standards is prepared by dilution in a normal human serum treated by ion exchange and free of $T_4$. The standard curve is drawn up with the aid of 250 µl samples containing 50 µl of N-AANS solution 50 µl of human serum free of $T_4$ or 50 µl of one of the $T_4$ µstandards 100 µl of APC-$T_4$ tracer 100 µl of antibody/cryptate conjugate The samples to be assayed have the same composition except that the 50 µl of standard are replaced with 50 µl of the individual serum to be assayed.

The assay is performed in 96-well microplates (Dynatech, USA).

After incubation for 30 min at room temperature, the results are read on a laser fluorimeter such as that described in Example 1, equipped with a 665 nm filter with a width at half-height of 20 nm, using a 1000 Hz flash lamp as the excitation source for 1 s, over a time window of 100 µs and after a delay of 50 µs.

The values obtained for each standard (B) are divided by the value of the standard 0 ($B_o$) and expressed as a percentage (B/$B_o$%). The concentration of the samples to be assayed is calculated by comparison with the standard curve.

The results are reported in Table V below:

TABLE V

| Thyroxin ng/ml | B/$B_o$ % |
|---|---|
| 0 | 100 |
| 10 | 91 |
| 20 | 82.6 |
| 50 | 61.7 |
| 100 | 43.3 |
| 250 | 23 |

The results show that the values obtained vary proportionately to the concentration of $T_4$. The presence of sodium fluoride in the measuring medium makes it possible to ensure the sensitivity of the measurement in a serum medium.

EXAMPLE 9

Assay of the 19.9 antigen

The 19.9 antigen is a carbohydrate representative of carcinoma of the colon.

As the site for the anti-19.9 antibody is a repetitive epitope, the same antibody is labeled either with the donor or with the acceptor.

This homogeneous immunoassay is carried out using antibody/Eu TBP and antibody/APC conjugates prepared in a manner analogous to that described in Example 4.

The 19.9 antigen and the anti-19.9 antibody are supplied by Centochor, USA.

The two conjugates are diluted in 100 mM phosphate buffer, NaF 150 mM, HSA 1 g/l, pH 6.

A standard range of 19.9 antigen is prepared by diluting a concentrated solution of antigen in newborn calf serum.

The following are added successively to 96-well polystyrene microplates (Dynatech, USA):

50 µl of standard solution of 19.9 antigen

50 µl of dilution buffer

100 µl of antibody/Eu TBP conjugate at 0.5 g/ml

100 µl of antibody/APC conjugate at 5 g/ml

After incubation for 3 h 30 min at room temperature, the results are read with the aid of the laser fluorimeter described in Example 1, equipped with a 650 nm filter with a width of 20 nm, after a delay of 50 µs and over 400 µs.

The results are reported in Table VI below and expressed in arbitrary units (AU):

TABLE VI

| 19.9 antigen u/ml | Signal AU |
|---|---|
| 0 | 312 |
| 9 | 419 |
| 30 | 572 |
| 64 | 890 |
| 138 | 1602 |
| 278 | 2491 |

These results show that the measured signal varies proportionately to the amount of 19.9 antigen in the medium.

The presence of sodium fluoride in the measuring medium again makes it possible to carry out the measurement with a high degree of sensitivity.

EXAMPLE 10

Assay of carcinoembryonic antigen (CEA)

This homogeneous immunoassay uses two monoclonal antibodies, G12 and G15 (CIS bio international, France), coupled respectively with the europium cryptate Eu TBP and allophycocyanin.

The two conjugates, G12/Eu TBP and G15/APC, are diluted in 100 mM phosphate buffer, HSA 1 g/l, NaF 150 mM.

The following are added successively to polystyrene microplates (Dynatech, USA):

100 µl of standard solution

100 µl of G12/cryptate conjugate at 0.5 µg/ml

100 µl of G15/APC conjugate at 5 µg/ml

After incubation for 3 h at 37° C., the results are read with the aid of the laser fluorimeter described in Example 1, equipped with a 650 nm filter with a width of 20 nm, after a delay of 50 µs and over 400 µs.

The results obtained are reported in Table VII below and expressed in arbitrary units (AU):

TABLE VII

| CEA ng/ml | Signal AU |
| --- | --- |
| 0 | 345 |
| 5.9 | 420 |
| 21 | 474 |
| 72 | 769 |
| 2634 | 1058 |

The results show that the emitted signal varies proportionately to the concentration of CEA. Furthermore, amplification of the signal makes it possible to detect the CEA with a sensitivity of the order of ng/ml.

The presence of sodium fluoride in the measuring medium again makes it possible to carry out the measurement with a high degree of sensitivity.

What is claimed is:

1. A method of reducing interference in a fluorescent assay of an analyte using at least one fluorescent compound as the tracer, which comprises adding fluoride ions to the measuring medium.

2. A method according to claim 1 wherein the fluorescent tracer used is a rare earth chelate or cryptate.

3. A method according to claim 1 or claim 2 wherein the measuring medium is a biological medium.

4. A method according to claim 3 wherein the measuring medium is a serum medium.

5. A method according to claim 3 wherein sodium, cesium, potassium or lithium fluoride is added to the measuring medium.

6. A method according to claim 5 wherein the measuring medium is a serum medium and the concentration of sodium fluoride added to said medium is 50 to 500 mM/l.

7. A method according to claim 5 wherein the measuring medium is a serum medium and the concentration of potassium fluoride is 50 mM/l to 5M/l.

8. A method for reducing interference in the measuring medium during a fluorescent method of detecting and/or determining an analyte in a medium which may contain it comprising adding fluoride ions to the measuring medium.

9. A method according to claim 8 wherein said method is a homogeneous fluorescent method.

10. A method according to claim 8 or claim 9 wherein said method is a fluorescent method comprising:
   a) adding to said medium a first reagent constituted of at least one specific receptor for said analyte,
   b) adding a second reagent selected from the group consisting of
      the analyte and
      one or more receptors specific for said analyte, one of the first or second reagents being coupled with a fluorescent donor compound, and the other reagent being coupled with a fluorescent acceptor compound, and the order of addition of the first and second reagents being reversible,
   c) incubating the resulting medium either after the addition of each reagent or after the addition of both reagents,
   d) exciting the resulting medium at the excitation wavelength of the donor compound, and
   e) measuring, at equilibrium or under kinetic conditions, the signal emitted by the fluorescent acceptor compound.

11. A method for reducing interference in the measuring medium during a fluorescent method of detecting and/or determining an analyte in a medium which may contain it, consisting of adding fluoride ions to the measuring medium, comprising:
   a) adding, to said medium containing the analyte in question, a first reagent consisting of at least one receptor specific for said analyte, coupled with a fluorescent donor compound,
   b) adding a second reagent consisting of one or more other receptors specific for said analyte, said second reagent being coupled with a fluorescent acceptor compound,
   c) incubating said medium either after the addition of each reagent or after the addition of both reagents,
   d) exciting the resulting medium at the excitation wavelength of the fluorescent donor compound by means of a light source, and
   e) measuring the signal emitted by the fluorescent acceptor compound.

12. A method according to claim 10 wherein said method is a competitive method comprising:
   a) adding, to said medium containing the analyte in question, a first reagent consisting of a receptor specific for said analyte, coupled with a fluorescent donor compound,
   b) adding a second reagent made up of the analyte coupled with a fluorescent acceptor compound,
   c) incubating said medium either after the addition of each reagent or after the addition of both reagents,
   d) exciting the resulting medium at the excitation wavelength of the fluorescent donor compound, and
   e) measuring the signal emitted by the fluorescent acceptor compound.

13. A method according to claim 10 wherein said method is a competitive method comprising:
   a) adding, to said medium containing the analyte in question, a first reagent consisting of a receptor specific for said analyte, said receptor coupled with a fluorescent acceptor compound,
   b) adding, as a second reagent, the analyte being coupled with a fluorescent doner compound,
   c) incubating said medium either after the addition of each reagent or after the addition of both reagents,
   d) exciting the resulting medium at the excitation wavelength of the fluorescent donor compound, and
   e) measuring the signal emitted by the fluorescent acceptor compound.

14. A method according to claim 10 wherein the first reagent and second reagent are added simultaneously to the medium containing the analyte in question.

15. A method according to claim 10, wherein the same receptor, either coupled with a luminescent donor compound or with a luminescent acceptor compound, is respectively used as the first reagent and as the second reagent.

16. A method according to claim 10 in which the fluorescent donor compound is a rare earth chelate or cryptate.

17. A method according to claim 16 in which the rare earth cryptate is a terbium or europium cryptate.

18. A method according to claim 17 wherein the donor compound is the terbium cryptate Tb trisbipyridine or the europium cryptate Eu trisbipyridine.

19. A method according to claim 10 wherein the fluorescent donor compound is a europium cryptate and the fluorescent acceptor compound is selected from the group consisting of allophycocyanin, allophycocyanin B, phycocyanin C or phycocyanin R.

20. A method according to claim 10 wherein the fluorescent donor compound is a terbium cryptate and the fluorescent acceptor compound is selected from the group consisting of rhodamines, thionine, phycocyanin R, phycoerythrocyanin, phycoerythrin C, phycoerythrin B or phycoerythrin R.

* * * * *